United States Patent [19]
Kleinmeyer

[11] Patent Number: 5,530,369
[45] Date of Patent: Jun. 25, 1996

[54] METHOD FOR MONITORING THE FLOW AND CURE RATE OF A RESIN MATERIAL USING TIME ENCODED PULSES

[75] Inventor: James Kleinmeyer, Aberdeen, Md.

[73] Assignee: The United States of America as represented by the Secretary of the Army, Washington, D.C.

[21] Appl. No.: 314,989

[22] Filed: Sep. 29, 1994

[51] Int. Cl.⁶ .......................... G01N 27/00; G01R 27/02
[52] U.S. Cl. .......................... 324/676; 324/71.1; 324/690
[58] Field of Search .......................... 324/71.1, 663, 324/676, 690, 710, 712, 713, 649, 724; 340/524, 525, 825.10, 825.14, 825.20, 825.79, 604, 605, 632

[56] References Cited

U.S. PATENT DOCUMENTS

| | | | |
|---|---|---|---|
| 3,383,863 | 5/1968 | Berry | 61/1 |
| 4,423,371 | 12/1983 | Senturia et al. | 324/663 |
| 4,777,431 | 10/1988 | Day et al. | 324/690 |
| 5,164,675 | 11/1992 | Howe et al. | 324/690 |
| 5,210,499 | 5/1993 | Walsh | 324/649 |
| 5,357,202 | 10/1994 | Henderson | 324/715 |
| 5,418,551 | 5/1995 | Ise | 345/174 |

*Primary Examiner*—Kenneth A. Wieder
*Assistant Examiner*—Diep Do
*Attorney, Agent, or Firm*—Freda L. Krosnick; Frank J. Dynda

[57] ABSTRACT

A digital sensor network scanner for use in monitoring resin flow and its cure progress during a resin fabrication process in which a plurality of non-intersecting electrically conductive threads are arranged in a grid-like configuration with each sensor thread having a sensor input for a sensor data path so as to create a plurality of sensors is disclosed in which a first section of the scanner supplies time encoded pulses to the sensor input path. A second section of the sensor network scanner includes a plurality of detectors which are connected to the sensor data path as well as to a plurality of LEDs and which are also triggered by the same time encoded pulses applied to the sensor input path. When a sensor data path is in a conducting state, the applied time encoded pulses propagate down the sensor data path to the detector which, having simultaneously received a signal from both the network scanner and the sensor, illuminates the LED.

4 Claims, 3 Drawing Sheets

METHOD FOR MONITORING THE FLOW AND CURE RATE OF A RESIN MATERIAL USING TIME ENCODED PULSES

BACKGROUND OF THE INVENTION

The present invention relates to a device for the integration of a large number of sensors that share a common data path. More particularly, the present invention relates to a digital interrogation system for use with a sensing grid system which is used to obtain data from a plurality of sensors used in connection with monitoring the flow and cure rate of a resin material.

The ability to produce a composite material having specified properties is of great importance in a variety of military, as well as commercial fields. Being able to monitor the production of these materials in order to assure the presence of the essential properties required for a specific purpose would be a significant advancement in the composite material art. Monitoring the production of resin material to make sure that it has certain, unique properties such as strength, stiffness and weight, or combinations of those properties, would enable material scientists to better develop the materials needed. Such monitoring would allow one skilled in the composite material art to successfully produce a material needed with less waste, and with the ability to identify any unfavorable properties of the composite material while it is in the production stage, instead of in the testing stage. It also allows for variations in the production process to be made in the early stages of development.

The prior art teaches the use of fiber optics for detecting damage in composite structures. Hofer, in an article entitled "Fiber Optic Damage Detection in Composite Structures," *Composites,* Volume 18, No. 4 (September, 1987), describes a method for inspecting a composite material for remote damage. The method described utilizes surface mounted or embedded fiber optic cables. The fiber optic cables can be drawn out to diameters comparable to that of the composite material reinforcement. Hence, the fiber optic cables can be embedded permanently in the composite without significantly influencing the overall integrity or properties of the composite material. Although the present invention may be adapted for use with the fiber optic cables described in the article, nowhere in the article is it taught that the fiber optic arrangement therein provides a means for determining resin location and cure during composite fabrication. Moreover, nowhere in the article is the grid-like system used with the present invention set forth. The fiber optic system described in the Hofer article does not possess the novel features within the scope of the present invention.

A wide variety of devices already exist for monitoring the curing process of a wide range of resin materials. Those existing devices utilize a variety of dielectric or microdielectric techniques to measure the electrical resistance or capacitance of the resin material being produced. The information obtained by those prior art techniques is then passed to a series of conventional signal conditioners, computer hardware and software. The conventional signal conditioners, computer hardware and software then interpret that information and display it in a fashion which illustrates the curing process of the resin materials.

Prior art in composite monitoring utilizes the basic, conventional dielectric and microdielectric techniques. Those techniques have been available, and have been used in the art for quite some time. Some patents illustrating the use of those well-known techniques are discussed in U.S. Pat. No. 5,210,499 to Walsh, the disclosure of which is incorporated herein.

The sensors taught in the patents discussed in U.S. Pat. No. 5,210,499 to Walsh cannot be incorporated into the composite materials to be monitored in large numbers because of the size, cost, and limited means of, attachment. Since those sensors cannot be incorporated into, the materials in large numbers, the uniformity of properties of the composite material being produced cannot be accurately monitored. Moreover, the prior art sensors, even if they could be incorporated into the composite materials in large numbers, are prohibitively expensive; therefore, an alternate monitoring apparatus and method must be considered.

Berry, U.S. Pat. No. 3,383,863, teaches a method of detecting leaks in a pond, tank and pit. Berry makes use of a grid of electrical wires wherein the resistance between different wires of the grid are measured. It appears that the grid of electrical wires in that reference need not intersect with one another as one would expect in a conventional grid configuration. Note column 2, lines 65–70. Although Berry appears to teach the specific grid-like configuration used with the present invention, nowhere does the reference suggest employing such a grid-like sensor to monitor resin flow or resin cure. Moreover, Berry makes use of an ohmmeter. The use of the monitoring apparatus of the present invention, i.e., a scanner and/or computer device, are not even remotely suggested by the teachings in Berry.

The present invention offers an apparatus and method that is convenient, because of its use of conventional, electrically conductive, sensor threads; inexpensive, because of its maximizing the use, of each sensor thread; and reliable. The sensing grid used with the present invention can be imbedded not only in the composite reinforcement, but it can be part of the bleeder, breather, and bagging materials as well. The invention provides a means for monitoring resin migration during autoclave, hot press and other prepreg composite processes. The present invention also provides a means for evaluating and monitoring thorough wet-out and cure, as well as a means for determining optimum mold and process configurations of the composite resin materials as they are being produced. Furthermore, the device can provide three-dimensional flow field information, as well as local resin flow front velocities.

The present invention makes use of, for example, the electrically conductive threads in a set grid-like configuration as disclosed in U.S. Pat. No. 5,210,499 to Walsh. The cost of performing the monitoring function is, therefore, kept to a minimum. To date, only the Walsh patent has disclosed an instrument for monitoring the cure of a wide range of resin systems using sensors that are incorporated as integral components of the composite resin structure. The present invention is directed to an improved device for utilizing a sensor system having a grid-like array of non-intersecting electrically conductive threads or other materials to serve as leads that can be connected to the instant sensor network scanner.

The present sensor network scanner overcomes the disadvantages inherent in the device disclosed in the Walsh patent. For example, the multiplexer/rapid switching system, scanner and computer system disclosed in that patent requires expensive up front costs as well as substantial additional costs in order to expand its monitoring capabilities to larger grids. In addition, the system disclosed in the Walsh '499 patent operates relatively slowly and is not practical for real time applications having large parts and sensor grids.

The present sensor scanning system, on the other hand, is a portable solid state digital scanning system whose scanning speed is accomplished much more quickly and requires much less cost than prior art systems to expand to larger parts and sensor grids. The instant invention is intended for use, as a device to interrogate a network of interconnected sensors that share a common data path. Such sensors must operate either by making or breaking a connection as a result of changes which occur in the sensor environment. The present invention provides a fast and efficient means with which to interrogate the sensor system and allows the output to be displayed visually or to be made available to a host computer.

In addition to the advantages discussed above, the sensor network scanner of the present invention operates independently of a computer but can easily be interfaced to or implemented in software on a computer. Further, due to the symmetry of the design and the modular nature of the disclosed sensor network scanner, the instant scanner can be readily expanded to include additional sensors with minimal circuit revision and at low cost.

SUMMARY AND OBJECTS OF THE INVENTION

In view of the foregoing, it should be apparent that there still exists a need in the art for an apparatus for sequentially scanning a network of interconnected sensors that share a common data path in which electronic means are utilized in a simple and precise manner to accomplish a substantial reduction in the processing time needed for scanning all of the sensors.

More particularly, it is an object of this invention to provide a sensor network scanner as aforementioned having simple and reliable electronic circuitry which does not require costly components or extensive circuit modifications to be expanded to scan large grids.

Still more particularly, it is an object of this invention to provide a sensor network scanner which utilizes a scanning section and timing coded pulses to scan the sensor data paths.

Another object of the present invention is to provide a reliable, portable and relatively inexpensive sensor network scanner for use in interrogating a network of interconnected sensors that share a common path.

Briefly described, these and other objects of the invention are accomplished by providing a digital sensor network scanner consisting of two sections. The first section is the scanner section, which supplies timing encoded pulses to the sensor input path. The second section of the inventive sensor network scanner consists of a plurality of detectors which are connected to both the scanner section and to plurality of LEDs. At the same time that the scanner circuit applies a timing encoded pulse to a sensor input path, that same pulse is simultaneously used to trigger the corresponding detector circuit for that same input path. If the sensor along the sensor data path is in a conducting state, then the pulse is propagated down the sensor data path to the detector. When the, detector has simultaneously received signals from both the scanner and the sensor, then an LED corresponding to the sensor is activated. The same signal used to trigger the LED may also be sent to a host computer for further control of the molding process. In that manner, multiple sensors are quickly scanned using time encoded pulse propagation.

With these and other objects, advantages and features of the invention that may become hereinafter apparent, the nature of the invention may be more clearly understood by reference to the following detailed description of the invention, the appended claims and to the several drawings attached herein.

DETAILED DESCRIPTION OF THE PREFERRED EMBODIMENT

Figure 1:
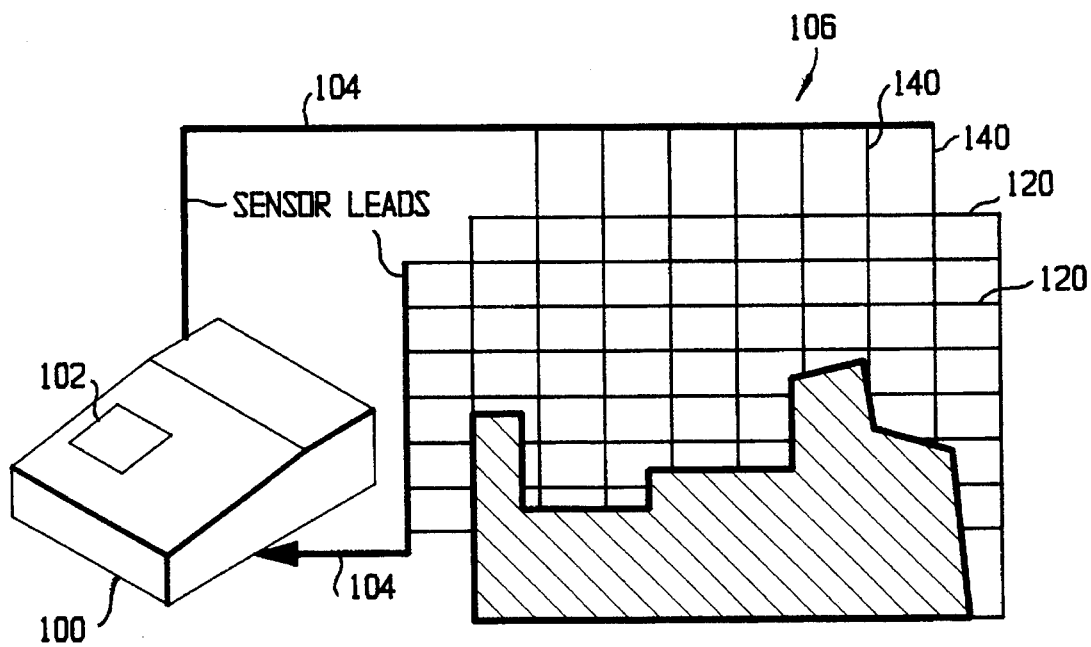
FIG. 1 is a pictorial drawing of a network of interconnected sensors to which the sensor network scanner apparatus of the present invention is connected.

Referring now in detail to the drawings wherein like parts are designated by like reference numerals throughout, there is illustrated in FIG. 1 the sensor network scanner 100 of the present invention, which includes a preferred LED display 102 or an LCD or other type of display 102 for indicating the condition of the scanned sensor paths. The sensor network scanner 100 of the present invention is connected by means of leads 104 to a grid-like monitoring apparatus 106 which is formed from a plurality of electrically conductive threads 120 and 140 formed in a non-intersecting grid-like configuration. It should also be understood, however, that, in addition to electrically conducting threads, optical fibers could likewise be utilized. It should further be understood that the sensor network scanner 100 of the present invention is designed to operate with the SMART weave system disclosed in the Walsh '499 patent.

Other types of sensors which can be utilized in addition to those disclosed above include conducting or semi-conducting fibers, wires or other materials placed in a grid mesh with porous non-conducting material placed between orthogonal conducting pairs. Similarly, air or other inert gas could be used to fill a gap between orthogonal conducting pairs. Then, in the presence of some conducting material which fills the space between the conducting fibers, the circuit is completed and the detector is activated.

Figure 2A:
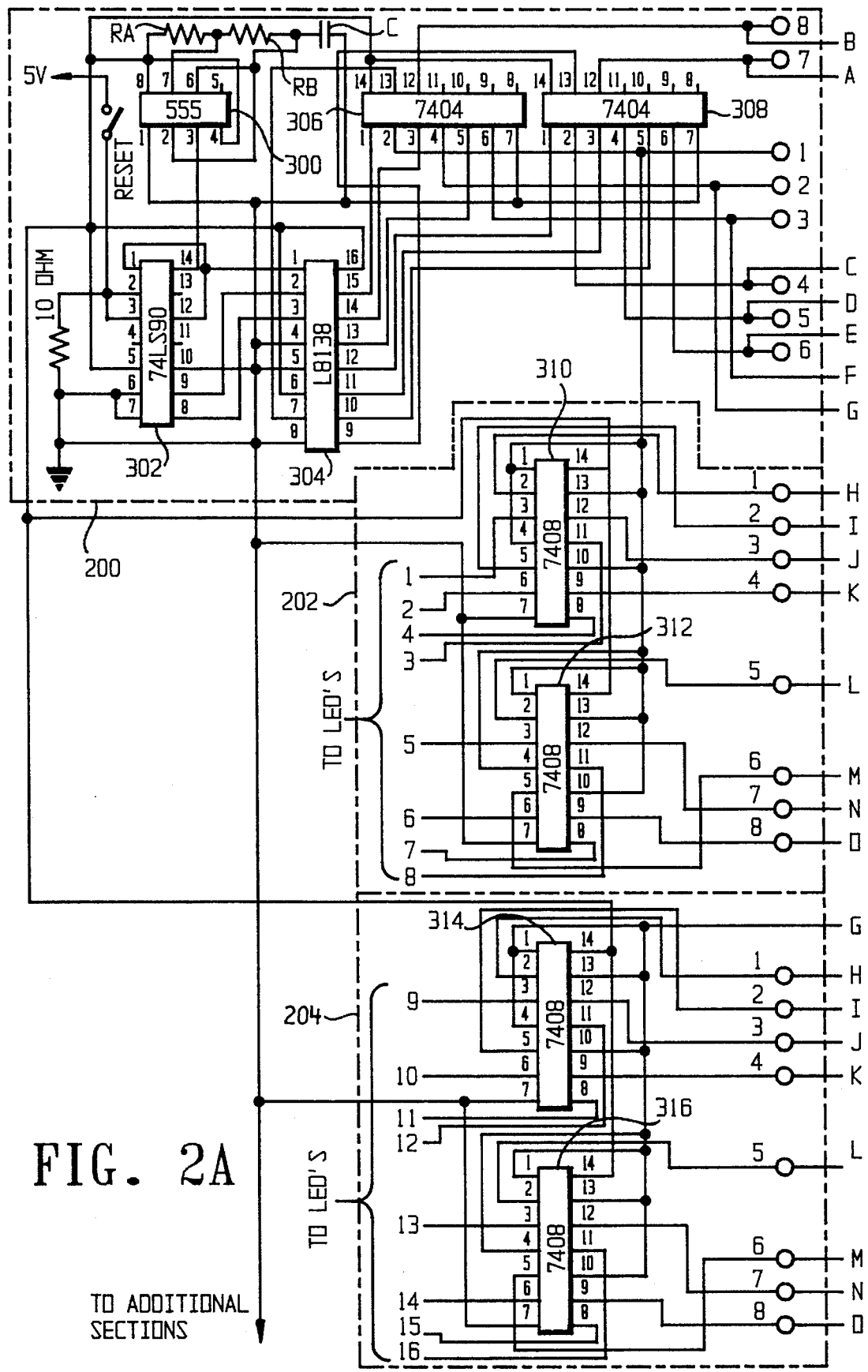
FIGS. 2A–2B are an electrical schematic diagram of the circuitry of the sensor network scanner apparatus of the present invention.
Figure 2B:
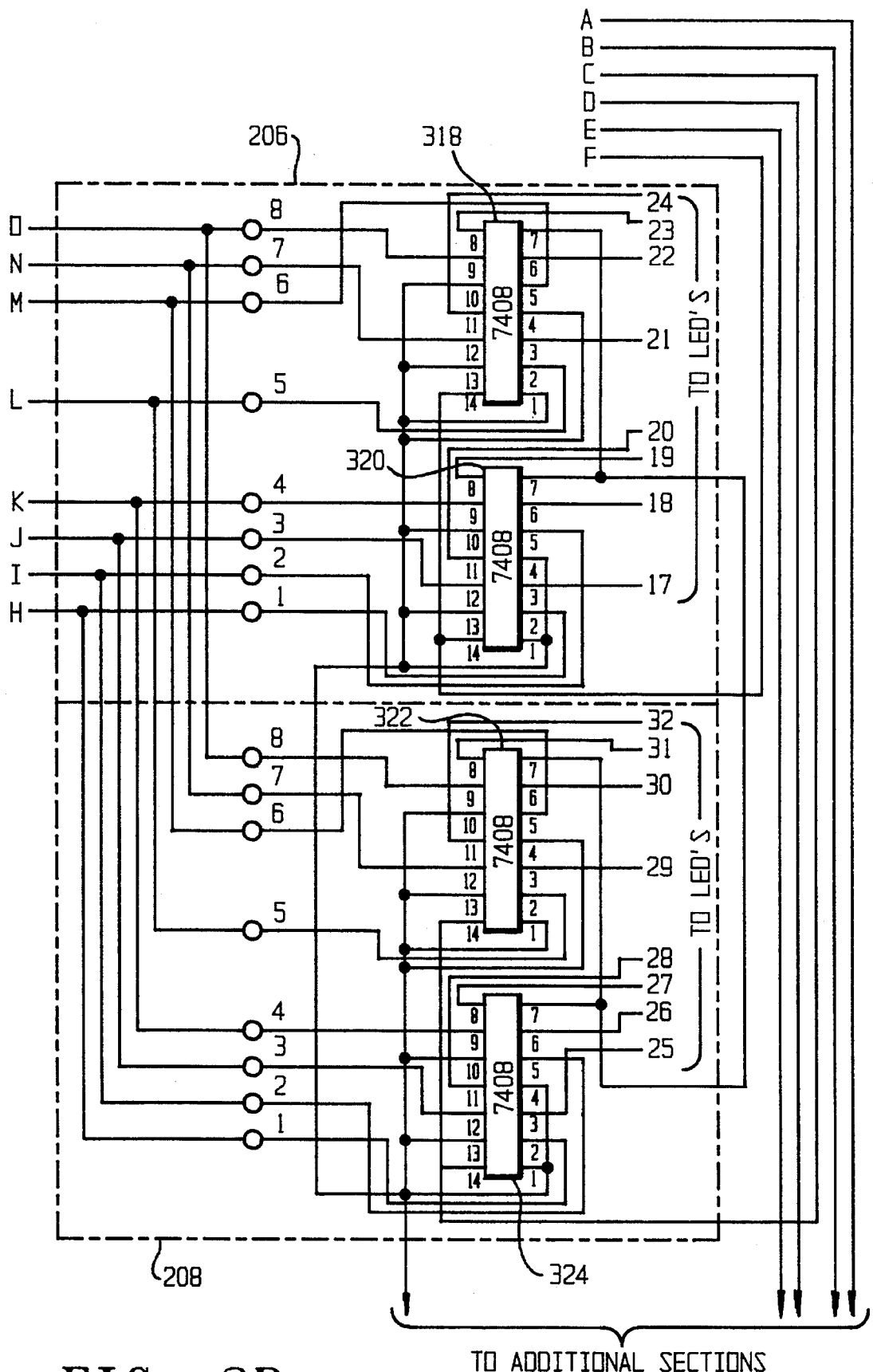

FIGS. 2A–2B illustrate an electrical schematic diagram of the circuitry utilized with the network sensor scanner apparatus 100 of the present invention. As previously discussed, the sensor network scanner 100 of the present invention is comprised of a scanner section 200 which generates a series of time encoded pulses, each of which is applied to a different sensor data path. The scanner circuitry 200 utilizes a standard model 555 single TTL compatible timing circuit, such as a MC1455 integrated circuit, which is capable of producing accurate timing delays or oscillations. The 555 timing IC 300 is operated in an astable mode such that the timer provides a precise free running oscillation whose frequency and duty cycle are controllable by a single external capacitor C and two external resistors $R_A$ and $R_B$. The timing circuit 300 may be triggered and reset on falling waveforms and the output structure can source or sink up to 200 mA or can be used to drive MTTL circuits. This timing circuit 300 is inexpensive, is a direct replacement for NE555 timer chips, and it is readily known to those of ordinary skill in the art how to calculate the oscillation frequency and duty cycle and thus no further explanation of that timing circuit 300 is believed to be necessary.

The scanner circuitry 200 also utilizes a 4-bit ripple-type decade counter 302, which may preferably be a model 74LS90 integrated circuit. As is well known, that integrated circuit consists of four master-slave flip-flops which are internally connected to provide a divide-by-five section and a divide-by-two section. Each section has a separate clock input to initiate state changes of the counter on the High to Low clock transition. In addition, a gated AND asynchronous master reset is provided which overrides both clocks and resets or clears all of the flip-flops. By setting a TTL level signal of +5 volts across the master reset inputs, pins 2 and 3, a counter reset can be invoked, forcing the scanner stage 200 and detector stages 202–208 to restart the scan.

The counter reset feature is useful for synchronizing the instant sensor system to external events, such as computer control and data storage. Since the output from the divide-by-two section of the decade counter 302 is not internally connected to the succeeding stage of that counter, the counter device 302 must be configured to operate in a predetermined desired mode.

In the sensor network scanner of the present invention, in order to operate as a BCD counter, the pin 1 input must be externally connected to the pin 12 output of the decade counter 302. The pin 14 input of the decade counter 302 receives the incoming count from pin 3 of the timer circuit 300, thus producing a BCD counting sequence. Typically, the maximum frequency obtainable for the counter circuit 302 is chip limited to 42 Mhz. That provides a scanning frequency that is more than sufficient for most sensor sampling rates. However, as will be obvious to those of ordinary skill in the art, by upgrading the integrated circuits utilized to faster CMOS or similar chip technology, increased sampling rates will result, where necessary.

The BCD counting sequence generated by the counter 302 is then used to drive the model 74LS138 decoder circuit 304. This connection is made through the output pin numbers 12, 9 and 8 of the counter circuit 302 which are connected to the input pins 1, 2 and 3 of the decoder circuit 304. The decoder circuit 304 accepts the 3 binary weighted inputs from the counter circuit 302 and, when enabled (pins 4 and 5 of the decoder circuit 304 are tied to ground and pin 6 is tied to a TTL level signal of +5 volts), will provide eight mutually exclusive, active LOW outputs at pins 7 and 9–15. The decoder circuit 304 features three enable inputs, namely two active LOW inputs and one active HIGH input. That multiple enable function allows for the easy parallel expansion of the decoder circuit to a one of 32 decoder in the case of large sensor networks.

Because the outputs of the decoder circuit 304 are active LOW, an inverter circuit is required. Each of the model 74LS04 hex inverter circuits 306 and 308 provide six TTL compatible inverter circuits. By utilizing the two hex inverter circuits 306 and 308, each of the eight active LOW outputs from the decoder circuit 304 are able to be inverted. The outputs from each of the inverters 306, 308, at pins 2, 4, 6 and 12, are used to provide the necessary enable signals for each of the detector modules 202–208 as well as for the sensor grid. It should be noted, however, that for wiring simplicity, the inverter circuits of pins 8 and 10 were not used in the circuitry as shown in FIGS. 2A–2B.

The eight active LOW outputs from the 74LS138 TTL 1 of 8 decoder circuit 304 are connected to the corresponding eight hex inverter inputs at pins 1, 3, 5 and 13, where four inverters from each of the inverter chips 306 and 308 are used. That results in eight mutually exclusive, time sequenced active HIGH outputs at terminals 1–8 of the inverter circuits 306, 308. Those eight leads are connected to the eight sensor input grid lines 120 and 140 as well as to the inputs of each of the eight detector modules. (Only four detector modules 202–208 are shown. The other four detector modules are formed from the same circuitry as the detector modules 202–208.)

Each of the detector circuits 202–208 utilizes two model 74LS08 quad 2 input AND Gates 310–324. Each of the quad AND Gates includes four TTL compatible AND Gate circuits. By using two of the quad AND Gates in each of the detector circuits 202–208, a single AND Gate circuit is provided for each of the eight corresponding sensor grid leads, shown as element 120 in FIG. 3. Each of the AND Gate circuits and each of the integrated circuits provides an active HIGH output signal, only when both of its inputs are simultaneously active HIGH. At all other times, the output of each AND Gate circuit is active LOW. One of the eight active HIGH outputs at the terminals 1–8 of the scanner circuit 200 is used to trigger each of the eight TTL compatible AND Gate circuit inputs at pins 1, 4, 10 and 13 for each pair of the quad AND Gate integrated circuits 310–324. The remaining eight AND Gate input pins 2, 5, 9 and 12 are connected to the eight sensor output grid lines 120, as shown in FIG. 3.

Each of the AND Gate output pins 3, 6, 8 and 11 for each of the quad AND Gate integrated circuits 310–324 is connected to an LED or similar device (not shown). The result is that each AND Gate reports an active HIGH signal (by lighting the appropriate LED or similar device) only when it has simultaneously received active HIGH signals from both the scanner circuitry 200 and the appropriate sensor output lead.

Figure 3:
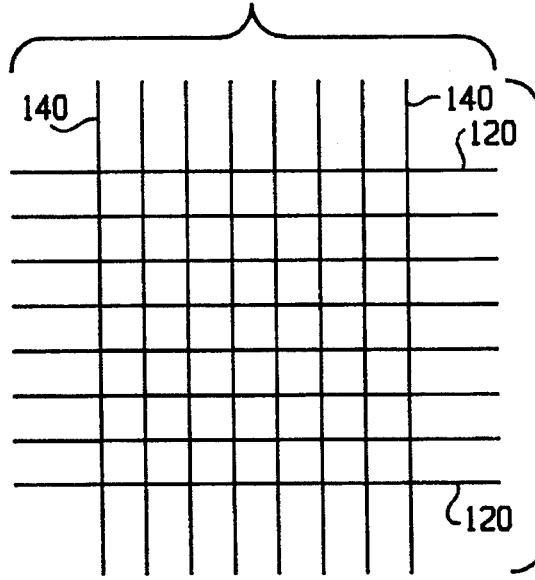
FIG. 3 is an electrical schematic drawing of the network of interconnected sensors used with the network scanner apparatus of the present invention.

FIG. 3 shows an electrical schematic drawing of the sensor grid shown in pictorial form in FIG. 1. The grid is made up of eight non-intersecting conducting pairs which, in the presence of a conducting medium such as resin, completes a circuit between each of the pairs 140 and 120.

As shown in FIG. 3, each of the sensor inputs 1–8 are connected to the terminals 1–8 from the scanner circuit 200. Each of the grid lines 120 is connected to one of the eight sensor outputs connected to each of the detector modules 202–208.

In order to monitor a matrix of sensors 140, 120 larger than 8×8, the system of the present invention can be expanded. For example, if the goal is to add additional sensor output lines, then additional 74LS08 AND Gate integrated circuits are introduced to each new sensor output line (one or more sensor output lines to each two chip detector modules). In addition, the inverted timing signal from the 74LS138 decoder/demultiplexer integrated circuit 304 is connected to one of each of the AND Gate inputs of the additional AND Gate integrated circuits and each of the additional sensor output lines 120 is connected to the remaining input of each of the additional AND Gate inputs so that the additional sensors may be scanned. In addition, the output of each of the AND Gate integrated circuits must be added to the LED display in order to provide visualization of the data stream.

If additional scanner lines are required, then the decoder circuit 304 must be expanded in order to provide additional mutually exclusive, time sequenced active HIGH outputs. As discussed above in connection with the discussion of the scanner circuitry 200, the decoder integrated circuit 304 may be expanded via the three enable lines to become a 1 of 32 bit decoder. Such procedure is well documented in the specification sheets provided by the manufacturer of the integrated circuit and thus need not be discussed here. Once complete, additional hex inverter circuits 306, 308, are also required in order to bring the output of the decoder 304 to an active HIGH state.

If both of the above-described procedures are carried out, then the sensor scanning system of the present invention may be expanded to accommodate, for example, a 32×32 sensor grid. For larger sensor grids, the sensor network scanner circuit may be duplicated, except for the timer circuit 300, which is used to provide a common clock for the entire scanner in order to ensure a synchronized system. The second scanner circuit may then be connected to the next consecutive 32×32 sensor grid as discussed before. The clock pulse from the timer circuit 300 will then be gated with the last active HIGH time encoded output signal from the previous sensor network scanner circuit. That will trigger the next sensor network scanner circuit to pick up with the sensor where the previous scanner circuit ended. The process of chaining the sensor network scanner circuits may be continued in 32×32 modules until the desired grid size has been achieved.

Even though, for any given sensor output, there could be multiple grid connections made from any sensor input, the sensor scanner system of the present invention is able to interrogate each one individually. That is due to the fact that, at any given clock cycle, only one sensor input line is active and all sensor output connections are being monitored by the appropriately triggered detector circuit 200–208. It is also important to note that, for cases where the conductive medium used to form the sensor junctions has a "low end" characteristic impedance, for example, copper, silver, etc., such as that might be found in metal doped epoxy resins, the sensor input current should be kept sufficiently low such that the scanner circuit current flowing with the impedance of only one sensor junction will trigger the appropriate detector integrated circuit 310–324. As a practical matter, the voltage resulting from the scanner circuit after it passes through two or more grid junctions should be less than two volts, which is the active HIGH level input voltage for the quad AND Gate integrated circuits 310–324.

As shown in FIGS. 2A and 2B, the scanner circuitry 200 utilizes control logic to send pulses out over eight enable lines connected to the terminals indicated as 1–8. The detector circuitry modules 202–208 utilize 74LS08 TTL logic gates to detect the presence of a signal. The TTL logic gates are connected such that the encoded pulses sent out over the eight enabled lines trigger those logic circuits such that they then await the resulting pulse which has propagated down the sensor path being tested. The outputs from each of the 74LS08 logic circuits are connected as indicated to LEDs in order to indicate the status of the tested sensor. Alternatively, the same signal output by the 74LS08 logic gates to trigger each of the LEDs may also or alternatively be sent to a host computer (not shown) for further processing or for use in further controlling the molding process.

Although only a preferred embodiment is specifically illustrated and described herein, it will be appreciated that many modifications and variations of the present invention are possible in light of the above teachings and within the purview of the appended claims without departing from the spirit and intended scope of the invention.

What is claimed is:

1. A method for monitoring the flow and cure rate of a resin material during a resin fabrication process in which a plurality of electrically conductive sensor threads arranged in a non-intersecting, grid-like configuration so as to become embedded within said resin material and so as to create a plurality of sensor gaps, with each sensor gap comprising the space between an input sensor thread and an output sensor thread which is a sensor thread perpendicular to said input sensor thread in said grid-like configuration, wherein said input sensor thread, said sensor gap, and said output sensor thread comprise a sensor data path; comprising the steps of:

pumping a resin material into a monitoring device having said electrically conductive sensor threads arranged in a non-intersecting, grid-like configuration so as to create a plurality of sensor gaps;

generating a plurality of time encoded pulses;

applying each of said generated plurality of time encoded pulses to a different said input sensor thread;

connecting each one of a plurality of detecting circuits to a different one of said output sensor threads;

triggering each one of said plurality of detecting circuits using said generated plurality of time encoded pulses; and detecting receipt of said time encoded pulses by any of said plurality of detecting circuits of said time encoded pulses wherein receipt of said time encoded pulse by any of said plurality of detecting circuits is indicative of resin flow and cure in one of said plurality of sensor gaps.

2. The method of claim 1, further including the step of indicating receipt by one of said plurality of detecting circuits of one of said time encoded pulses using a light emitting diode.

3. The method of claim 2, further including the step of arranging a plurality of said emitting diodes in a pattern corresponding to said grid-like configuration of said plurality of sensor gaps.

4. The method of claim 1 wherein triggering each one of said plurality of detecting circuits using said generated plurality of time encoded pulses synchronizes each of said plurality of detecting circuits to avoid detecting said time encoded pulses from other of said sensor data paths.

\* \* \* \* \*